United States Patent [19]

Moyers et al.

[11] Patent Number: 5,440,133

[45] Date of Patent: Aug. 8, 1995

[54] CHARGED PARTICLE BEAM SCATTERING SYSTEM

[75] Inventors: Michael F. Moyers, Redlands; Jeffrey V. Siebers, Grand Terrace, both of Calif.

[73] Assignee: Loma Linda University Medical Center, Loma Linda, Calif.

[21] Appl. No.: 102,770

[22] Filed: Aug. 6, 1993

Related U.S. Application Data

[63] Continuation-in-part of Ser. No. 87,196, Jul. 2, 1993, abandoned.

[51] Int. Cl.$^6$ .............................................. H01J 33/00
[52] U.S. Cl. ............................... 250/492.3; 250/505.1
[58] Field of Search ........................... 250/492.3, 505.1

[56] References Cited

U.S. PATENT DOCUMENTS

| | | |
|---|---|---|
| 2,629,831 | 2/1953 | Atchley, Jr. |
| 3,604,931 | 9/1971 | Kastner et al. |
| 3,901,588 | 8/1975 | Longhenry |
| 4,020,356 | 4/1977 | Brahme ................. 378/149 |
| 4,095,114 | 6/1978 | Taumann ............... 250/505.1 |
| 4,347,440 | 8/1982 | Haas ...................... 250/505.1 |
| 4,392,239 | 7/1983 | Wilkens ................. 378/146 |
| 4,463,266 | 7/1984 | Brahme ................. 250/505.1 |
| 4,868,843 | 9/1989 | Nunan ................... 378/152 |
| 5,019,713 | 5/1992 | Shmidt .................. 250/492.3 |
| 5,054,048 | 10/1991 | Wang .................... 378/146 |

FOREIGN PATENT DOCUMENTS

| | | |
|---|---|---|
| 7511033 | 11/1975 | France. |
| 63-249578 | 10/1988 | Japan ..................... 250/505.1 |

OTHER PUBLICATIONS

Koehler et al. "Flattening of Proton Dose Distributions for Large-Field Radiotherapy", Medical Physics, vol. 4, No. 4, Jul./Aug. 1977, pp. 297-301.

Cova et al. "Critical Considerations of Employing Scatterers with Electron Beams Accelerated by the Betatron", Strahlentherapie 133, 1967, pp. 7-11.

Brahme et al. "Optimization of Proton and Heavy Ion Therapy Using Adaptive Inversion Algorithm", Radiotherapy and Oncology, vol. 15, 1989, pp. 189-197.

Bjarngard et al. "Electron Scattering and Collimation System for a 12-MeV Linear Accelerator", Medical Physics, vol. 3, No. 3, 1976, pp. 153-158.

Svensson, "Influence of Scattering Foils, Transmission Monitors ad Collimating System on the Absorbed Dose Distribution From 10 to 35 MeV Electron Radiation", (unknown source) submitted for publication Oct. 22, 1970, pp. 443-453.

G. Sandberg, "Electron Beam Flattening with an Annular Scattering Foil", IEEE Transactions on Nuclear Science, 1973, pp. 1025-1026.

Marbach et al. "Optimization of Field Flatness and Depth-Dose for Therapy Electron Beams", Phys. Med. Biol, vol. 26, No. 3, 1981, pp. 435-443.

Mandour et al. "Systematic Optimization of the Double-Scatterer System for Electron Beam Field-Flattening", Strahlentherapie 154, 1978, pp. 328-332.

Kozlov et al. "Forming of Electron Beams from a Betatron by Foil Scatterers", Acta Radiologica Therapy Physics Biology 15, 1976, pp. 493-512.

Kozlov et al. "Application of Scattering Foil Systems for Forming Large-Sized Uniform Electron Therapy Fields", Strahlentherapie 158, 1982, pp. 432-439.

M. F. Moyers et al. "A Continuously Variable Thickness Scatterer for Proton Beams Using Self-compensating Dual Linear Wedges", Medical Physics or Nuclear Instruments and Methods, 1992.

(List continued on next page.)

Primary Examiner—Jack I. Berman
Attorney, Agent, or Firm—Knobbe, Martens, Olson & Bear

[57] ABSTRACT

A radiation treatment apparatus comprises a source of charged particles, preferably protons, for producing a particle beam, and a scattering foil for changing the diameter of the charged particle beam. The scattering foil is configured so that its thickness is both uniform and continuously adjustable throughout a range of thicknesses.

22 Claims, 6 Drawing Sheets

OTHER PUBLICATIONS

Therapy", poster-board presented at the 1992 American Association of Physicists in Medicine conference, Aug. 1992, 23 pages.

Gottschalk, "Proton Radiotherapy Nozzle with Combined Scatterer/Modulator", 2nd International Charged Particle Workshop and meeting of the Proton Therapy Co-Operative Group, Loma Linda Univ. Med. Ctr. Loma Linda, California, Oct. 1987.

B. Gottschalk, "Double-Scattering System with Optimum Dose Uniformity in Proton Radiotherapy", Aug. 1, 1986.

Brahme, "Electron Transport Phenomena and Absorbed Dose Distributions in Therapeutic Electron Beams", 14th International Congress of Radiology, Rio de Janeiro, Brazil, Oct. 24-29, 1977.

A. Montelius and A. Brahme, "Charged Particle Beam Flattening Using an Optimized Dual Scattering Foil Technique".

J. V. Siebers and D. W. Miller, "Passive Scattering System Design Optimization for Proton Radiation

CHARGED PARTICLE BEAM SCATTERING SYSTEM

This is a continuation-in-part of parent patent application, Ser. No. 08/087,196, filed Jul. 2, 1993, inventors Michael F. Moyers and Jeffrey V. Siebers, and entitled "Proton Beam Scattering System," now abandoned.

FIELD OF THE INVENTION

The present invention is related to a radiation treatment apparatus utilizing scattering to produce a continuously variable penetration radiation beam and a method of treating a patient by directing the radiation beam onto a treatment field within said patient.

BACKGROUND OF THE INVENTION

Conventional radiation therapy utilizes electron beams and x-rays as a means of treating and controlling cancer. Due to the inability of current technology to preferentially deposit the radiation at the site of the cancer, healthy tissues between the tissue surface and the cancer also receive high doses of radiation and, thus, are damaged. Consequently, physicians use a less-than-optimal dose to reduce the undesirable damage to healthy tissues and the subsequent side effects. In many cases, this proves to be an unacceptable alternative.

Proton therapy has proven to be a viable alternative to x-ray and electron beam therapy in cancer treatment. By offering greater precision than conventional radiation therapy, physicians are able to deliver higher, more effective doses to target volumes. Protons tend to travel through the body tissue without significant absorption until they reach a specific point within the body. At this point, which corresponds to the Bragg peak of the proton beam, the proton energy is released. Accordingly, when the Bragg peak of the proton beam corresponds with the target location to be treated, the target location receives the highest concentration of radiation. There is very little lateral secondary scatter and, thus, virtually no damage to surrounding healthy tissues. While the Bragg peak for monoenergetic proton beams permits the energy deposited by the beam to be concentrated at a particular site within the patient, the proton beam is typically only a few millimeters wide, which is insufficient for delivering a sufficient radiation treatment dose to irregularly-shaped three-dimensional treatment volumes, such as tumors, particularly if the treatment volumes are large.

Thus, there is a need for a radiation treatment system which will accurately and reproducibly deliver maximum, uniform radiation treatment to designated target volumes.

SUMMARY OF THE INVENTION

The present invention provides a novel scattering system for charged particles which allows depth dose tailoring using spill to spill energy extraction while maintaining field uniformity. The preferred embodiment of this invention includes a source of charged particles which produces a beam of charged particles having an intensity and energy which varies with time. A scattering foil is placed in the path of the particle beam for changing the diameter of the particle beam and, thereby, covering the target volume.

The beam intercept portion of the scattering foil provides a uniform thickness which is continuously adjustable through a range of thicknesses. The scattering system is comprised of first and second scatterers. The first scatterer is comprised of a pair of parallel and opposing tapered wedges. The wedges are made of a high z material (e.g. lead, gold, . . .), which contains high atomic number atoms that generate scattering but do not change the energy (i.e. do not significantly change the range). Each wedge slides back and forth on rails or shafts and is controlled by a motor and position control unit, so that equivalent sections of the wedges overlap at the beam intercept portion.

The second scatterer is mounted on a carousel and intercepts the path of the particle beam at a location downstream from the first scatterer. The second scattering foil is made of both high z material and low z material. The low z material (e.g. plastics made of carbon) contains low atomic number atoms that do not generate much scattering but do reduce the energy. The high atomic number material has a cross-sectional profile that is approximately gaussian in shape. The low atomic number material surrounds the high atomic number material and, directly beneath it, has a hollowed-out portion which has a mating profile that is approximately gaussian in shape.

The invention also includes a controller which adjusts the energy of the particles in the beam at the source. In addition, a patient collimator and a bolus, configured to the irregular three-dimensional shape of the tumor, is used to vary the penetration range of the particles within the particle beam as a function of the radial distance of the particles from the propagation axis of the beam.

During operation of this scattering system, the protons are generated by the source, a particle accelerator, typically a synchrotron, and impinge onto the first scatterer. After being scattered by the wedges, the proton beam has a nearly gaussian fluence profile. The first scatterer, therefore, provides only part of the total scattering needed, the rest being provided by the second scatterer. The beam emerging from the second scatterer is broad at the patient location with both a uniform range and a uniform fluence profile.

DETAILED DESCRIPTION OF THE INVENTION

Figure 1:
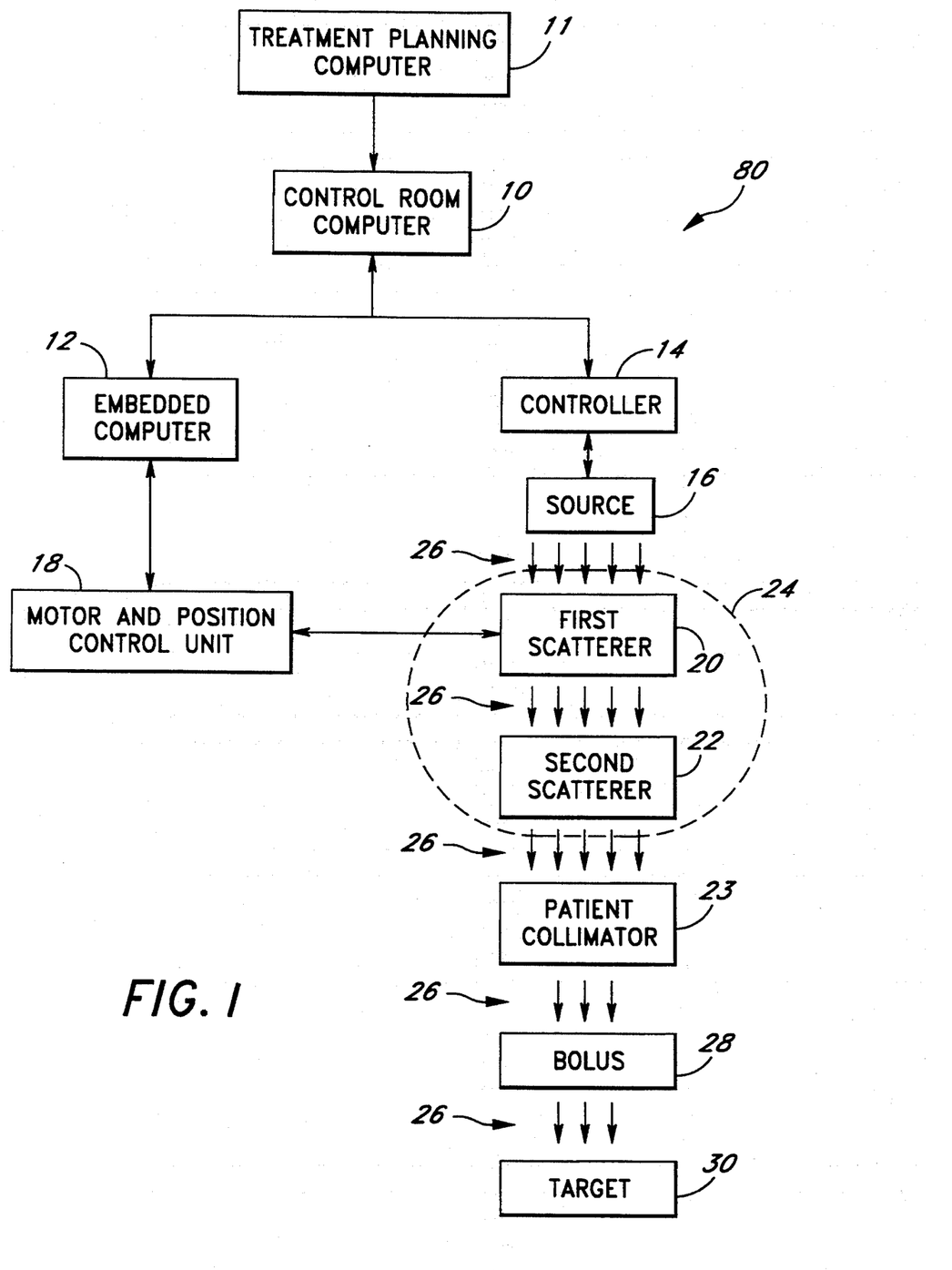
FIG. 1 is a schematic view of the charged particle beam therapy system.

Referring to FIG. 1, in the preferred embodiment of the invention, a control room computer 10 is in direct communication with an embedded computer 12 and a controller 14. The controller 14 and the embedded computer 12 transmit the appropriate signals to a source 16 and a motor and position control unit 18, respectively. The motor and position control unit 18, in turn, controls the positioning of a first scatterer 20. The first scatterer 20, in combination with a second scatterer 22, make up one embodiment of a scattering system 24, which scatters a beam 26 of particles emitted by the source 16. Finally, the resulting beam 26 of particles is shaped by a patient collimator 23, partially absorbed by a bolus 28, and impinges on a specified target 30 area located in a patient.

The source 16 comprises an accelerator, such as a synchrotron, that accelerates charged subatomic particles to energies which are useful for radiation treatment therapy. The synchrotron comprises a ring of energized magnets which produce a magnetic field. Particles, particularly protons, travel through the magnets in a vacuum tube. As the magnetic field in the ring is increased, the energy of the circulating protons also increases. The magnetic field continues to increase until it reaches a value which corresponds to a prescribed proton beam energy. At this point, the magnetic field is held constant and the protons are slowly extracted from the synchrotron. The energy range for a patient treatment may be, for example, a minimum of 70 MeV to a maximum energy of 250 MeV. The synchrotron is capable of accelerating protons to 70 MeV in one-quarter second and to 250 MeV in one-half second. The protons are emitted from the synchrotron in a gaussian-shaped beam.

A treatment planning computer 11 is used to plan a specific treatment necessary for each individual patient and provide the information used by the proton beam therapy device 80 during the patient treatment. The information is transferred from the treatment planning computer 11 to the control room computer 10 prior to delivering the radiation used in the patient's treatment. After being processed by the control room computer 10, the information is then sent to the embedded computer 12 and the controller 14.

The controller 14 receives the signals sent from the control room computer 10 and adjusts various accelerator parameters, such as the magnetic field of the magnets in the synchrotron, until the desired, corresponding proton beam energy is obtained. Thus, the controller 14 has the ability to increase or decrease proton acceleration via the ring of magnets. In addition, the controller 14 monitors the status of the source 16 and sends this information to the control room computer 10, which ultimately determines whether or not to terminate proton beam delivery.

Figure 2:
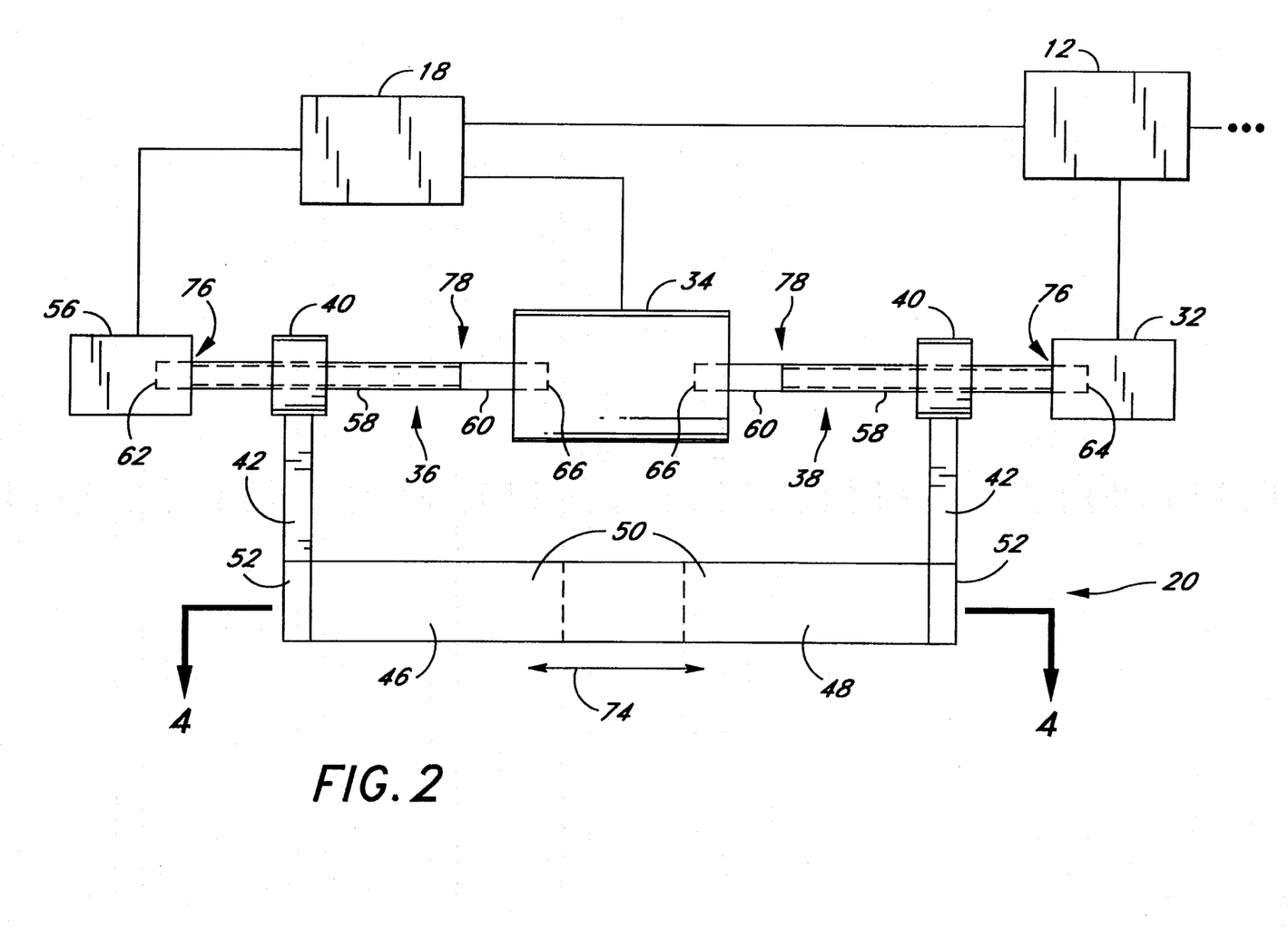
FIG. 2 is a partially schematic plan view of the motor and position control unit and the first scatterer.

The embedded computer 12 also receives commands from the control room computer and directly communicates this information to the motor and position control unit 18, shown in FIG. 2, which primarily controls the positioning of the first scatterer 20. Thus, the function of the embedded computer 12 is to continuously check the position of the first scatterer 20 via the motor and position control unit 18 and a verification encoder 32. In addition, the embedded computer 12 has the ability to terminate patient treatment by way of the control room computer 10 when the first scatterer 20 is no longer properly positioned.

FIG. 2 shows one embodiment of the motor and position control unit 18 and the first scatterer 20. In this embodiment, the embedded computer 12 is in direct communication with the motor and position control unit 18 and the verification encoder 32. The motor and position control unit 18 receives information from the embedded computer 12 and transmits the appropriate signals to a motor 34, that simultaneously rotates two identical shafts 36,38. Since the shafts 36,38 are identical, the following description will reference only the first shaft 36. A coupling 40 connects a bracket 42 to a shaft 36. A wedge 46, mounted on the bracket 42, is comprised of a scattering material 50 housed in a frame 52. A position encoder 56 monitors the position of a first wedge 46 via the number of rotations of the shaft 36 and sends the appropriate signals to the motor and position control unit 18. Next, the motor and position control unit 18 relays this information to the embedded computer 12, which verifies that the position of the first scatterer 20 is correct. The verification encoder 32, similar to the position encoder 56, verifies the position of a second wedge 48 by way of counting the number of rotations of the shaft 38, but relays this information directly to the embedded computer 12.

The shafts 36,38 are configured as cylindrical rods comprising a threaded section 58 and a non-threaded section 60. The threaded section 58 of each shaft 36,38 is incised with external continuous helical ribs or threads. The pitch of thread, which is measured in terms of the number of threads (or grooves) per unit of axial length, is identical on both shafts 36,38. A distal end 62 of the first shaft 36 extends into the position encoder 56, whereas a distal end 64 of the second shaft 38 extends into the verification encoder 32. A proximal end 66 of both shafts 36,38 extend into the motor 34.

Each shaft 36,38 is precisely made to provide a given linear displacement to each coupling 40 for each revolution. Thus, the spiral threads on each shaft 36,38 equally convert the rotary motion from the motor 34 into a linear movement of the couplings 40, which, subsequently, move the wedges 46,48 in unison. The motor and position control unit 18 controls the motor 34 rotations so that equivalent sections of the wedges 46,48 overlap, thereby presenting a uniform wedge thickness at the beam intercept portion 70, as shown in FIG. 4.

Figure 3:
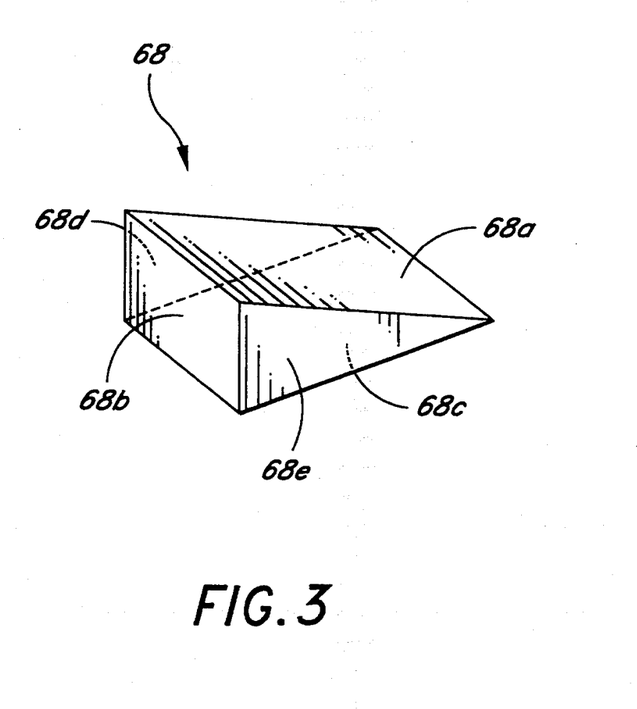
FIG. 3 is a perspective view illustrating one of the wedges of the first scatterer.

Referring to FIG. 3, for this embodiment, each wedge 46,48 comprises five flat or planar surfaces 68. Three of the surfaces 68a,68b,68c are four-sided or rectangular in shape, each side forming a 90° angle with its adjacent side; and, two of the surfaces 68d,68e are three-sided or triangular in shape, each triangular shaped surface having one 90° angle. Two of the rectangular shaped surfaces 68b,68c are at a 90° angle to each other, one surface 68c being in a plane parallel to the direction of motion 74, herewith designated as a parallel surface 68c, and the other surface 68b being in a plane orthogonal to the direction of motion 74, herewith designated as an orthogonal surface 68b. The remaining rectangular shaped surface 68a forms an inclined plane and is designated an inclined surface 68a. For this embodiment and for all intents and purposes, inclined means relative to the direction of movement 74 of the wedges. Each wedge is made of a high z-material, such as lead. A high z-material contains high atomic number atoms that generate scattering but do not change the energy of the particles.

Figure 4:
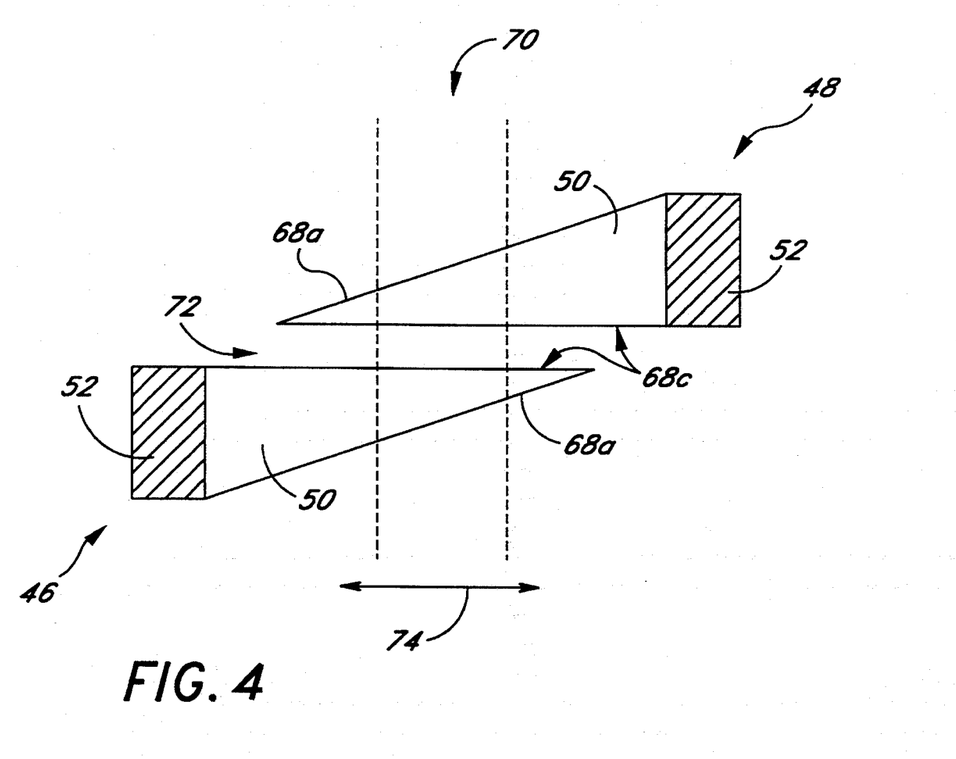
FIG. 4 is an elevational view in partial cross section taken along the lines 4—4 of FIG. 2 showing the wedges of the first scatterer.

Referring to FIG. 4, the wedges 46,48 are positioned so that their inclined surfaces 68a extend in opposite directions. The parallel surface 68c of the first wedge 46 lies in a plane parallel to a plane in which lies the parallel surface 68c of the second wedge 48. These planes, containing the wedges 46,48, are, thus, also parallel to the direction of motion 74 of the wedges 46,48. An air gap 72, of constant thickness, extends between the first wedge 46 and the second wedge 48. The wedges 46,48 are aligned so that the entire beam intercept portion 70 is of equal and uniform thickness of air gap 72 and scattering material 50. Thus, the wedges 46,48 may travel their entire length of motion/travel without colliding.

Referring back to FIG. 2, each coupling 40 travels the entire length of the threaded section 58 of the shaft onto which it is mounted. The threaded sections 58 are longer than the length of the non-inclined rectangular surfaces 68c of the wedges so that, when the couplings 40 are located at a threaded, distal end 76 of the shafts 36,38, the wedges 46,48 are positioned so that they do not overlap and no scattering material 50 is in the beam path 70. With the wedges in this position, no scattering occurs at the first scatterer 20. In contrast, the thickest amount of scattering material 50 is in the beam path 70 when frames 52 are adjacent to, but not within, the beam path 70. In this position, the couplings 40 are located at a threaded, proximal end 78 of the shafts 36,38. This particular configuration produces the greatest amount of scattering at the first scatterer 20. When the couplings 40 are located at some intermediate position on the threaded portion of the shafts 36,38, there is an intermediate amount of scattering material in the beam path and, consequently, an intermediate amount of scattering of the proton beam. Because of the wedge shaped first scatterer 20, an infinite choice of scattering material 50 thicknesses is available. Regardless of the choice, the combined thickness of the material 50 in the beam intercept portion 70 will be uniform. Due to this alignment and configuration of the first scatterer 20, all beams emerging from the beam intercept portion 70 of the first scatterer 20, regardless of the amount of scattering produced, will possess a basically gaussian shape.

Figure 5:
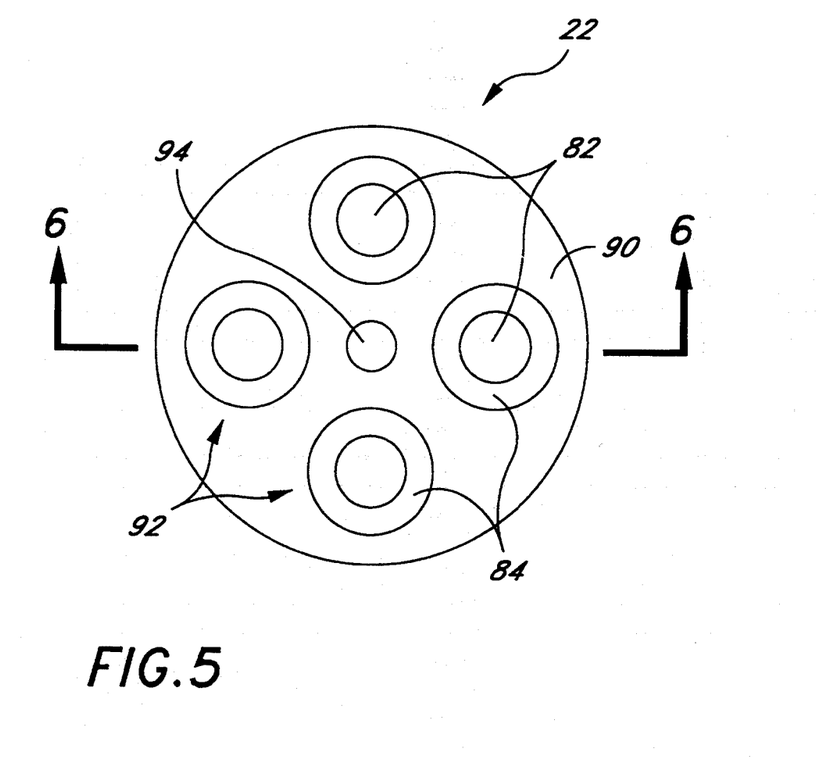
FIG. 5 is a plan view showing plural secondary scattering foils mounted in a carousel.
Figure 6:
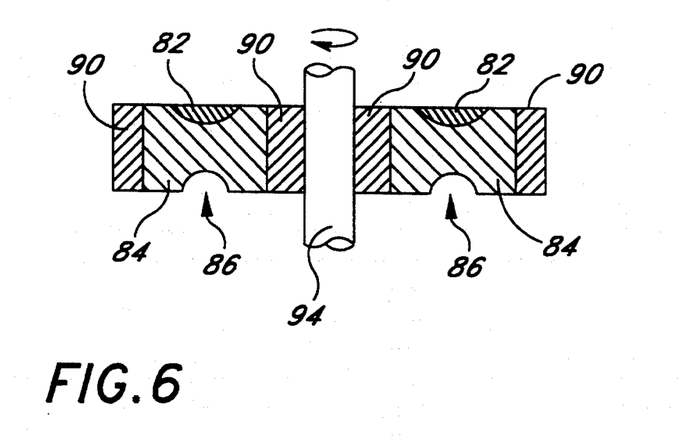
FIG. 6 is an elevation view in partial cross section taken along the lines 6—6 of FIG. 5 showing the plural secondary scattering foils.

The first scatterer 20, in combination with the second scatterer 22, comprises one embodiment of the scattering system 24 as shown in FIG. 1. The second scatterer 22, while not essential to the scattering system, is typically preferred under normal operating conditions in a proton beam therapy device 80. One embodiment for the second scatterer 22 of the scattering system 24 is shown in FIG. 5. For this embodiment, the wheel-shaped second scatterer 22 is comprised of a frusto-cylindrically shaped frame 90 housing a plurality of secondary scattering foils 92. Located in the center of the wheel-shaped second scatterer 22 is a rod 94. The rod 94 is used to mount the second scatterer 22 in the proton beam therapy device 80. The secondary scattering foils 92 are located equidistant from one another and from the rod 94. Each secondary scattering foil 92 is comprised of both high z material 82 and low z material 84. Referring to FIG. 6, the high z material 82 has a cross-sectional profile that is substantially gaussian in shape and is disposed within a hollowed-out portion 86 of the low z material 84. The low z material 84 (e.g. plastics made of carbon) contains low atomic number atoms that do not generate much scattering but do reduce the energy of each of the protons in the proton beam. The hollowed-out portion 86 has a substantially gaussian shaped surface that corresponds to the gaussian shaped profile of the high z material 82. In order to change the beam shape (i.e., profile of energy distribution) or amount of scatter from the secondary scattering foil 92, the second scatterer 22 is rotated around the rod 94 so that a different secondary scattering foil 92 is located in the path of the proton beam 26. Thus, FIG. 5 is one embodiment of the second scatterer; however, other suitable forms of the second scatterer, such as a second scatterer comprising six secondary scattering foils, may be suitable for some applications.

To obtain a plurality of proton beam scattering configurations, each secondary scattering foil 92 has a different configuration of high z material 82 and low z material 84. For example, one configuration of the secondary scattering foil 92 may include a large substantially gaussian shaped high z material 82, whereas another configuration may include a smaller substantially gaussian shaped high z material 82. In addition to changing the amount of high z material 84, the hollowed out portion of the low z material 82 may also be varied. For example, one configuration of the low z material 82 may include a large substantially gaussian shaped hollowed out portion, whereas another configuration may include a smaller substantially gaussian shaped hollowed out portion. Alternatively, the type of low z material 82 and high z material 84 may also be varied to obtain various proton scattering configurations. For example, a user may choose gold for a high z material 84 for one secondary scattering foil 92 and lead for the high z material 84 for another secondary scattering foil 92. Thus, the shape, amount and type of low z material 82 and high z material 84 may be varied to obtain numerous proton beam scattering configurations.

Referring back to FIG. 1, the proton beam therapy system also may include a patient collimator 23 and a bolus 28. The patient collimator 23 may be comprised of a thick plate made of lead alloy and an aperture with a periphery that shapes the cross section of the beam to match the configuration of target 30. As is well known, a bolus, such as the bolus 28, is a mass of material, usually plastic, that is configured in accordance with the irregular three-dimensional shape of the patient's tumor and anatomy. The bolus 28 is used to vary the penetration range of the particles within the particle beam 26 as a function of the radial distance of the particles from the propagation axis of the beam 26. After emerging from the bolus 28, the beam of particles 26 impinges on the target 30, which is the site of the tumor in the patient.

Figure 7:
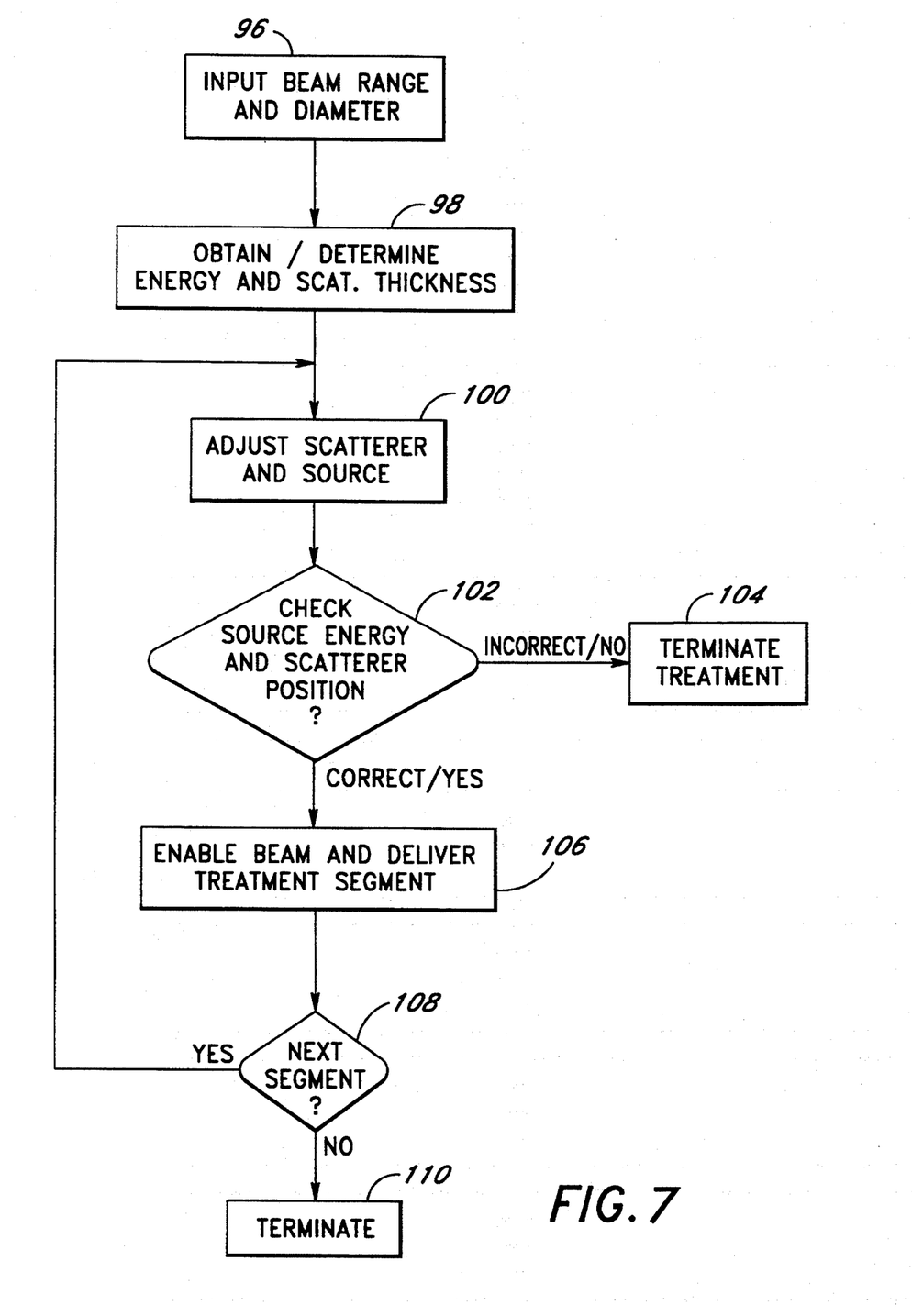
FIG. 7 is a flow chart illustrating the operation of the proton beam scattering system.

Operation of the proton beam therapy system is best illustrated in FIG. 7. During operation, a particular patient may receive the proton beam therapy treatment in sequential segments that comprise various combinations of parameters and these segments could be discrete (with intervals of time therebetween) or continuous. In any given treatment, parameters that may vary from one segment to the next include beam range, scatterer thickness, field radius and proton beam energy. Beam range refers to the depth of proton beam penetration into a patient, which may vary, depending on the treatment. The scatterer thickness refers to the thickness of the first scatterer 20 at the location where the beam 26 intercepts the scattering material 50, hereafter called the "beam intercept portion" 70. Field radius refers to the radius of the proton beam at a specified depth within the patient for a particular treatment. Proton beam energy refers to the energy of protons required to reach a specified depth within the patient at the target site. This information, beam range, scatterer thickness, field radius and proton beam energy, is determined for each segment of proton beam therapy treatment. Thus, for example, the treatment planning computer determines the desired beam radii and range of beam penetration required for a specific target volume site, as shown in activity block 96. The treatment planning computer 11 takes these values, and using a previously stored table of values, interpolates them to obtain the scatterer thicknesses and proton beam energies required for each segment of the treatment, as shown in activity block 98. This information is then sent to the control room computer 10 which, during treatment, relays the values to the controller 14 and the embedded computer 12 so that the appropriate signals are sent to adjust the energy emitted from the source 16 and the thickness of the first scatter 20, respectively, as shown in activity block 100. Next, the energy from the source 16 and the position of the first scatter 20 are verified, as shown in activity block 102, and, if incorrect, treatment is terminated, as shown in activity block 104. However, if the beam energy and scatterer position are correct, the beam is enabled and the treatment segment is delivered to the target, as shown in activity block 106. After the segment has been delivered, the system checks if there are additional segments, as shown in activity block 108. If additional segments exist, the appropriate values for the next segment are retrieved and the process is repeated. However, if no additional segments exist, treatment is terminated, as shown in activity block 110.

Figure 8:
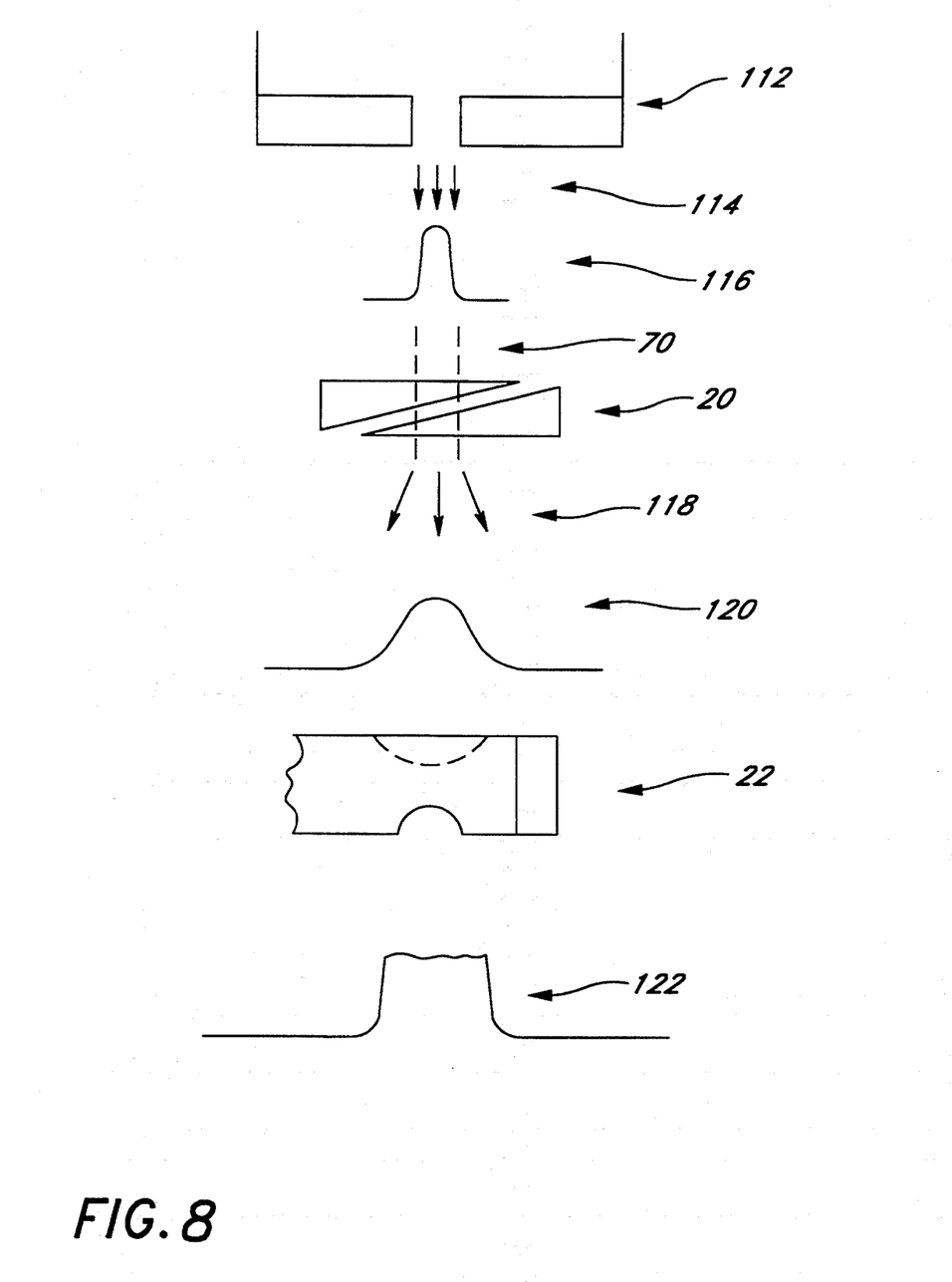
FIG. 8 is a schematic drawing illustrating the various beam profiles within the proton beam scattering system.

The shape of the proton beam energy distribution at various locations within the proton beam therapy system is illustrated in FIG. 8. Protons are generated by the accelerator and pass through a beam collimator 112, located immediately upstream of the wedges. The beam of protons 114 coming out of the collimator 112 has a narrow cross sectional width. Upon exiting the collimator 112, the beam 114 passes through the beam intercept portion of the first scatterer 20. The beam intercept portion 70 of the first scatterer 20 presents a uniform thickness of material over the entire area of the proton beam 114. Due to the particular configuration and material composition of the first scatterer 20, the scattered beam of protons 118 obtains a nearly gaussian fluence profile 120. Thus, the first scatterer 20 has increased the beam 114 diameter but the beam intensity is not uniform over the entire beam area. Further scattering of the beam 118 occurs as a result of passing through the second scatterer 22. Due to the particular design and material composition of the second scatterer 22, the profile of the beam 118 broadens and has a uniform range and uniform fluence profile 122. Thus, the diameter of the proton beam has been expanded to cover a substantial portion of the treatment field, while maintaining beam uniformity.

Referring again to FIG. 1, during operation of the proton beam therapy system, an operator mounts into the proton beam therapy device the bolus 28 corresponding to the three-dimensional shape of the patient's tumor. The bolus 28 is located between the second scatterer 22 and the patient/target 30. The scattering thicknesses and proton beam energy are obtained from the treatment planning computer for each of the various treatment segments. This information is then downloaded to the embedded computer 12 and the controller 14.

The controller 14 adjusts the source 16 until the appropriate proton beam energy is achieved. During this time, the embedded computer 12 sends the appropriate signals to the motor and position control unit 18 to properly position and verify the location of the wedges 46,48. The proper position corresponds to the required thickness in the beam intercept portion 70 of the first scatterer 20. Thus, the motor and position control unit 18 adjusts the first scatterer 20 until properly positioned and the desired thickness achieved.

Next, the source 16 and the motor and position control unit 18 sends back signals to the controller 14 and the embedded computer 12, respectively. If the appropriate beam energy and scatterer thickness are not achieved, the embedded computer 12 and the controller 14 sends a signal to the control room computer 10 to terminate the treatment. If, however, the signals from the embedded computer 12 and the controller 14 corresponded to information that the source 10 is at the appropriate energy level and the wedges 46,48 are properly positioned, the proton beam is enabled and treatment initiated.

After delivering the first treatment segment, the proton beam therapy system makes the appropriate adjustments to the beam energy and first scatterer thickness, if necessary, so the next treatment segment may be initiated. After all the segments have been delivered, treatment is terminated and the proton beam disabled.

The present invention may be embodied in other specific forms with out departing from its spirit or essential characteristics. The described embodiment is considered in all respects only as illustrative and not restrictive. The scope of the invention is, therefore, indicated by the appended claims rather than the foregoing description. All changes which come within the meaning and range of equivalency of the claims are to be embraced within their scope.

What is claimed is:

1. A radiation treatment apparatus, comprising:
 a source of charged particles which provides a charged particle beam; and
 a scattering foil in the path of the particle beam, said scattering foil being comprised of a high z material which substantially changes the diameter of the particle beam without substantially changing the energy of the particles, said beam intercepting said scattering foil at a beam intercept portion, said scattering foil having a thickness at said beam intercept portion of said scattering foil, said scattering foil being configured so that said thickness at said beam intercept portion is continuously adjustable through a range of thicknesses, the thickness of said scattering foil being uniform throughout said beam intercept portion through said range of thicknesses.

2. The apparatus of claim 1, additionally comprising a controller for adjusting the energy of the particles in said beam.

3. The apparatus of claim 1, additionally comprising a controller for adjusting the intensity of the beam.

4. The apparatus of claim 2, wherein said controller varies the energy of the particles in said beam at a location upstream of said scattering foil.

5. The apparatus of claim 4, wherein said controller is connected to said source so as to vary the energy of the particles in said beam at said source.

6. The apparatus of claim 1, additionally comprising an embedded computer which controls the thickness of said scattering foil.

7. The apparatus of claim 5, wherein said scattering foil comprises a first scatterer comprising a pair of wedges, and wherein the apparatus comprises an embedded computer which is connected to drive said wedges to vary the thickness of said scattering foil.

8. The apparatus of claim 1, wherein said scattering foil comprises a first scatterer comprising a pair of wedges, each having a taper.

9. The apparatus of claim 8, comprising a driver for relatively driving each of said wedges in a direction of said taper.

10. The apparatus of claim 7, additionally comprising a control room computer connected to said controller for adjusting the energy of the particles in said beam, said control room computer connected to said driver to adjust the position of said wedges in response to changes in the energy of the particles in said beam such that said diameter of said beam is maintained substantially constant.

11. The apparatus of claim 10, additionally comprising an embedded computer that controls the thickness of said scattering foil.

12. The apparatus of claim 2, additionally comprising a scatterer disposed in the path of said particle beam at a location downstream of said scattering foil.

13. The apparatus of claim 12, wherein said scatterer is comprised of both a low z material and a high z material, said scatterer comprising a carousel and a plurality of secondary scattering foils mounted on said carousel.

14. The apparatus of claim 12, wherein the controller varies the energy of the particles of said beam at a location upstream of both said scattering foil and said secondary scattering foils.

15. The apparatus of claim 1, additionally comprising a patient collimator with an aperture, said aperture having a periphery that shapes the beam laterally to the target.

16. The apparatus of claim 1, additionally comprising a bolus configured to vary the penetration range of particles within the particle beam as a function of the radial distance of the particles from the propagation axis of the beam.

17. The apparatus of claim 11, wherein said scattering foils are configured to produce a beam which has a substantially uniform fluence in a plane perpendicular to the axis of propagation.

18. The apparatus of claim 1, wherein said charged particles consist essentially of protons.

19. A method of treating a patient by directing radiation onto a treatment field within said patient, said method comprising:
producing a beam of charged particles having an energy which varies with time;
using a high z material to scatter at least some of said charged particles to provide an expanded beam having a cross-sectional area sized to cover at least a substantial portion of said treatment field, said scattering step comprising the step of directing the beam to intercept scattering material at a beam intercept portion of the scattering foil; and
controlling said scattering in accordance with the variations in the energy of said beam such that the size of the cross section of the expanded beam on the treatment field is substantially independent of said variations, said step of controlling comprising the step of adjusting the thickness of the scattering material within a range of thicknesses, while maintaining a uniform thickness of scattering material through the beam intercept portion.

20. The method of claim 19, wherein said expanded beam covers the entire treatment field.

21. The method of claim 19, wherein said producing step comprises producing a beam of protons.

22. The method of claim 19, additionally comprising the step of rotating a carousel comprising additional scattering material such that the beam passes through the additional scattering material.

* * * * *